United States Patent
Chang et al.

(10) Patent No.: US 9,244,018 B2
(45) Date of Patent: *Jan. 26, 2016

(54) PROBE HOLDING STRUCTURE AND OPTICAL INSPECTION DEVICE EQUIPPED WITH THE SAME

(71) Applicant: MPI Corporation, Chu-Pei, Hsinchu Shien (TW)

(72) Inventors: Chia-Tai Chang, Chu-Pei (TW);
Chin-Yi Tsai, Chu-Pei (TW);
Chiu-Kuei Chen, Chu-Pei (TW);
Chen-Chih Yu, Chu-Pei (TW);
Chien-Chang Lai, Chu-Pei (TW);
Chin-Tien Yang, Chu-Pei (TW);
Hui-Pin Yang, Chu-Pei (TW);
Keng-Shieng Chang, Chu-Pei (TW);
Yun-Ru Huang, Chu-Pei (TW)

(73) Assignee: MPI Corporation, Chu-Pei, Hsinchu Shien (TW)

( * ) Notice: Subject to any disclaimer, the term of this patent is extended or adjusted under 35 U.S.C. 154(b) by 164 days.

This patent is subject to a terminal disclaimer.

(21) Appl. No.: 13/940,870

(22) Filed: Jul. 12, 2013

(65) Prior Publication Data
US 2014/0016123 A1 Jan. 16, 2014

(30) Foreign Application Priority Data

Jul. 13, 2012 (TW) .............................. 101213567 U
Jul. 20, 2012 (TW) .............................. 101214087 U

(51) Int. Cl.
*G01N 21/88* (2006.01)
*G01R 1/04* (2006.01)
(Continued)

(52) U.S. Cl.
CPC ................. *G01N 21/88* (2013.01); *G01R 1/073* (2013.01); *G01R 1/07342* (2013.01); *G01R 1/04* (2013.01); *G01R 1/06711* (2013.01); *H01L 21/68* (2013.01)

(58) Field of Classification Search
CPC ..... G01N 21/88; G01R 1/073; G01R 1/07342
USPC ..................... 356/237.1–241.6, 242.1–243.8, 356/426–431, 600–640
See application file for complete search history.

(56) References Cited

U.S. PATENT DOCUMENTS 3,611,128 A * 10/1971 Nagata .......................... 324/72.5
3,723,013 A * 3/1973 Stirland et al. ............. 356/152.1
(Continued)

FOREIGN PATENT DOCUMENTS

CN 201203517 3/2009
JP 58-33700 B2 7/1983
(Continued)

*Primary Examiner* — Tri T Ton
*Assistant Examiner* — Jarreas C Underwood
(74) *Attorney, Agent, or Firm* — Muncy, Geissler, Olds & Lowe, P.C.

(57) ABSTRACT

A probe holding structure includes a substrate and a plurality of holding modules. The substrate has an opening and a plurality of grooves arranged around a periphery of the opening. The holding modules are connected with the grooves, respectively. Each holding modules includes a fixing member and a plurality of probes. The fixing member is connected with a corresponding groove. The probes are connected with the fixing member and pass through the corresponding groove. The probe holding structure is combined with a lens adjusting mechanism having a lens to form an optical inspection device for testing electric characteristics of chips.

24 Claims, 7 Drawing Sheets

(51) Int. Cl.
  *G01R 1/06*   (2006.01)
  *H01L 21/68*  (2006.01)
  *G01R 1/073*  (2006.01)
  *G01R 1/067*  (2006.01)

(56) References Cited

U.S. PATENT DOCUMENTS

| | | | | |
|---|---|---|---|---|
| 3,778,169 A | * | 12/1973 | Adams | 356/399 |
| 3,781,681 A | * | 12/1973 | Wagner | G01R 1/07342 324/72.5 |
| 4,480,223 A | * | 10/1984 | Aigo | G01R 1/07342 324/72.5 |
| 4,866,374 A | * | 9/1989 | Cedrone | G01R 1/0433 324/537 |
| 5,266,889 A | * | 11/1993 | Harwood et al. | 324/750.14 |
| 5,670,889 A | * | 9/1997 | Okubo | G01R 1/07342 324/755.05 |
| 5,751,157 A | * | 5/1998 | Kister | G01R 1/07342 324/750.25 |
| 5,959,461 A | | 9/1999 | Brown et al. | |
| 6,335,628 B2 | * | 1/2002 | Schwindt et al. | 324/750.19 |
| 7,256,591 B2 | * | 8/2007 | Tatematsu | G01R 1/07314 324/755.07 |
| 7,427,868 B2 | * | 9/2008 | Strid et al. | 324/755.03 |
| 7,579,849 B2 | * | 8/2009 | Kiesewetter et al. | 324/756.03 |
| 7,656,172 B2 | * | 2/2010 | Andrews et al. | 324/755.11 |
| 7,944,224 B2 | * | 5/2011 | Kister | 324/754.01 |
| 7,952,377 B2 | * | 5/2011 | Kister | G01R 1/07307 324/755.01 |
| 8,095,194 B2 | * | 1/2012 | Ninomiya et al. | 600/310 |
| 8,461,530 B2 | * | 6/2013 | Findlay et al. | 250/338.1 |
| 2007/0268486 A1 | | 11/2007 | Hagler | |
| 2014/0015561 A1 | * | 1/2014 | Chang | G01R 1/07342 324/756.03 |
| 2014/0016124 A1 | * | 1/2014 | Chang | G01N 21/88 356/237.1 |

FOREIGN PATENT DOCUMENTS

| | | |
|---|---|---|
| JP | H05-307049 | 11/1993 |
| JP | H09-274125 | 10/1997 |
| JP | H11-026521 | 1/1999 |
| JP | 2007-103787 | 4/2007 |
| JP | 2007-311515 A | 11/2007 |
| JP | 2011-0112421 A | 6/2011 |
| JP | 5577040 B2 | 8/2014 |
| TW | M356906 | 5/2009 |
| TW | I366672 | 6/2012 |
| TW | I375038 | 10/2012 |
| TW | I390209 | 3/2013 |
| TW | I390209 | 3/2013 |
| WO | 2004/053451 A1 | 6/2004 |
| WO | 2008/059767 A1 | 5/2008 |

* cited by examiner

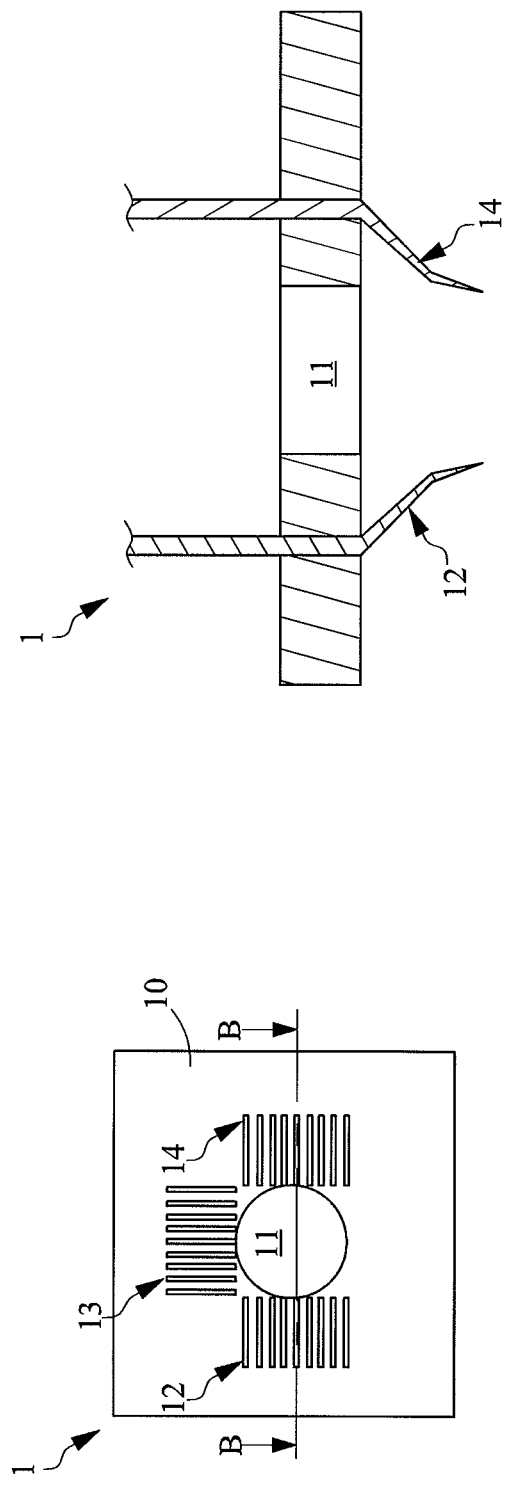
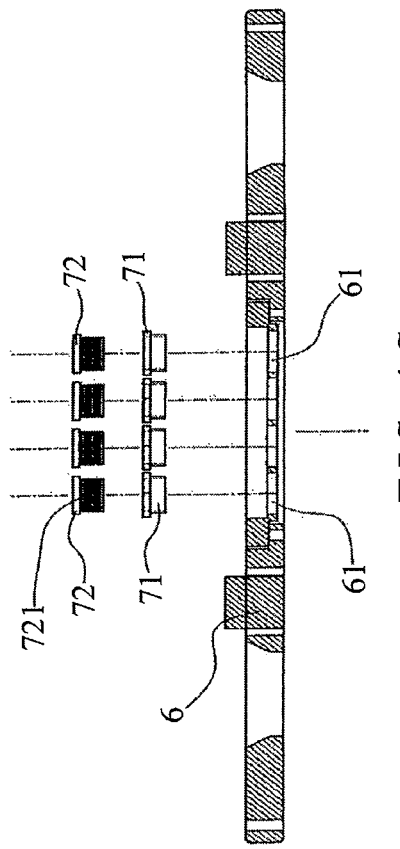
FIG. 1A PRIOR ART
FIG. 1B PRIOR ART
FIG. 1C PRIOR ART

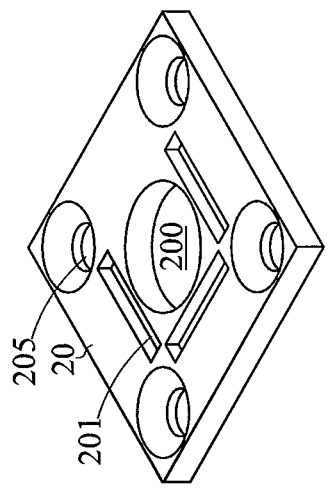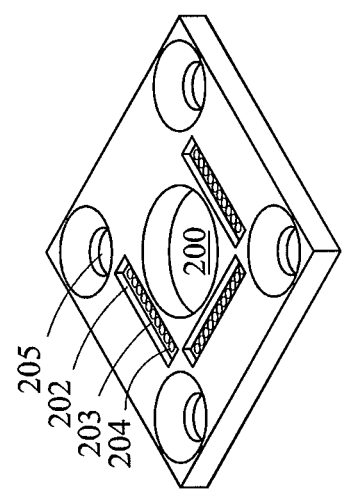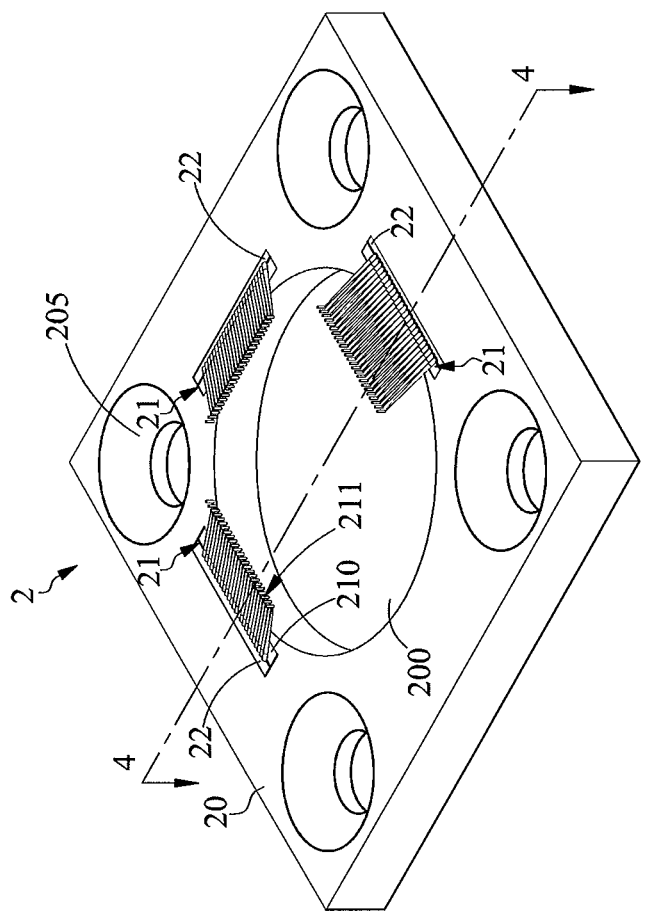

PROBE HOLDING STRUCTURE AND OPTICAL INSPECTION DEVICE EQUIPPED WITH THE SAME

CROSS-REFERENCE TO RELATED APPLICATIONS

This application claims priorities from Taiwan Patent Application No. 101213567 filed on Jul. 13, 2012 and Taiwan Patent Application No. 101214087 filed on Jul. 20, 2012, the entire contents of which are incorporated herein by reference.

BACKGROUND OF THE INVENTION

1. Field of the Invention

The present invention relates to probe holding and lens adjusting technologies and more particularly, to a combination-type probe holding structure and an optical inspection device equipped with the probe holding structure and a lens adjusting mechanism.

2. Description of the Related Art

In order to assure the quality of the product, a lot of testing tasks have to be conducted in production of semiconductor chips. One of the testing tasks is adapted to confirm whether the electric connections among the electronic components inside the semiconductor chip are good and the function of the chip is in compliance with specification of the quality control.

In a task of testing semiconductor chip, the tester needs to contact a device under test (DUT), such as a chip, through a probe card, and meanwhile the test result of the DUT can be obtained by conducting signal transmission and electric signal analysis. The aforesaid probe card is generally equipped with a plurality of fine-dimensional probes arranged in a certain pattern such that each probe may be aligned with a specific contact pad of the chip under test. When the probes contact the corresponding contact pads of the DUT respectively, they can positively transmit the test signals from the tester. In the meantime, the purpose of measuring the electric characteristics of the DUT can be achieved by the cooperation of the control and analysis processes of the probe card and the tester.

FIG. 1A is a schematic bottom view of a part of a probe card of a prior art, and FIG. 1B is a cross-sectional view taken along the line B-B of FIG. 1A. As shown in FIGS. 1A and 1B, the probe card 1 is composed of a guide plate 10 having an opening 11, and three series of probes 12, 13 and 14 arranged around a periphery of the opening 11. Because the guide plate 10 has a small area and a plurality of series of probes 12, 13 and 14 have to be mounted to the guide plate 10 with a limited area, the work of inserting the second and third series of probes 13 and 14 can not be simultaneously carried out with the process of inserting the first series of probes 12 upon manufacturing the probe card 1, resulting in decrease of the manufacturing efficiency of the probe card 1. In addition, in this prior art design, the probes are directly inserted through the guide plate 10. When the probe card 1 thus obtained has a manufacturing defect or one or more probes are malfunction in their contact operation, it is hard to fix the probe card by replacing the problematic probes separately, such that the guide plate mounted with the probes having problems are usually discarded, resulting in increase of the manufacturing cost.

FIG. 1C is a schematic lateral side view of a probing structure of a prior art used in a wafer-level testing. In this prior art design, the wafer-level probing structure is composed of a base seat 6 provided with a plurality of openings 61, each of which is adapted for accommodating a lens holder 71 therein. Each lens holder 71 is provided at an inside thereof with an accommodation for being screwingly coupled with a lens 72 through a thread 721. The disadvantage of this prior art design lies in that the position of the lens 72 can not be easily and precisely adjusted. Specifically speaking, each lens has a fixed focus and it is needed to let the focus of the lens be lain exactly on the device under test by adjusting the position of the lens, such that a clear image may generate. In the aforesaid prior art, the fine adjustment of the focus is carried out by adjusting the engagement relationship between the thread 721 on the periphery wall of the lens 72 and the thread provided inside the lens holder 71 so as to change the position of the lens 72 in the vertical direction. This adjusting work is however very inconvenient and adversely affects the probing efficiency. In addition, the backlash between the thread provided on the inner wall of the lens holder 71 and the thread 721 on the lens 72 will usually cause error in the position adjusting operation of the lens to adversely affect the optical image-forming effect.

In light of the above, it is desired to provide a combination-type probe holding structure and an optical inspection device having the probe holding structure and a lens adjusting mechanism to solve the problems of the above-mentioned prior arts.

SUMMARY OF THE INVENTION

The present invention has been accomplished under the circumstances in view. It is an objective of the present invention to provide a probe holding structure and an optical inspection device equipped with the same, wherein the probes are modularized and connected with the guide plate to increase the practicability of assembly of the probes and guide plate, enhance the manufacturing efficiency of the probe card, and make the replacement of the problematic probe possible and convenient so as to lower the manufacturing cost of the probe card.

It is another objective of the present invention to provide an optical inspection device further equipped with a lens adjusting mechanism, which is provided with threads and at least one adjustment notch at a top portion of a lens holder, such that the position of the lens holder carrying a lens therein can be simply adjusted by an adjustment jig.

To achieve the above-mentioned objectives, a probe holding structure provided by the present invention comprises a substrate and a plurality of holding modules. The substrate has an opening and a plurality of grooves arranged around a periphery of the opening. The holding modules are connected with the grooves, respectively. Each holding module comprises a fixing member and a plurality of probes. The fixing member is connected with a corresponding groove. The probes are connected with the fixing member and pass through the corresponding groove.

To achieve the above-mentioned objectives, an optical inspection device is further provided by the present invention, comprising a lens adjusting mechanism and at least one probe holding structure. The lens adjusting mechanism comprises a base seat having at least one first opening, and at least one lens holder received in the at least one first opening respectively and each having an accommodation for accommodating a lens. The at least one probe holding structure is disposed on a surface of the base seat. Each probe holding structure comprises a substrate and a plurality of holding modules. The substrate has a second opening and a plurality of grooves arranged around a periphery of the second opening. The holding modules are connected with the grooves, respectively. Each holding module comprises a fixing member connected with a corresponding groove, and a plurality of probes connected with the fixing member and passing through the corresponding groove.

BRIEF DESCRIPTION OF THE DRAWINGS

The present invention will become more fully understood from the detailed description given herein below and the accompanying drawings which are given by way of illustration only, and thus are not limitative of the present invention, and wherein:

FIG. 1A is a schematic bottom view of a part of a probe card according to a prior art;

FIG. 1B is a cross-sectional view taken along the line B-B of FIG. 1A;

FIG. 1C is a schematic lateral side view of a probing structure of a prior art used in a wafer-level testing;

FIG. 2 is a schematic perspective view of a probe holding structure according to an embodiment of the present invention;

FIGS. 3A and 3B are schematic perspective views showing two alternate forms of the substrate of the probe holding structure of the present invention;

DETAILED DESCRIPTION OF EMBODIMENTS

Figure 5A:
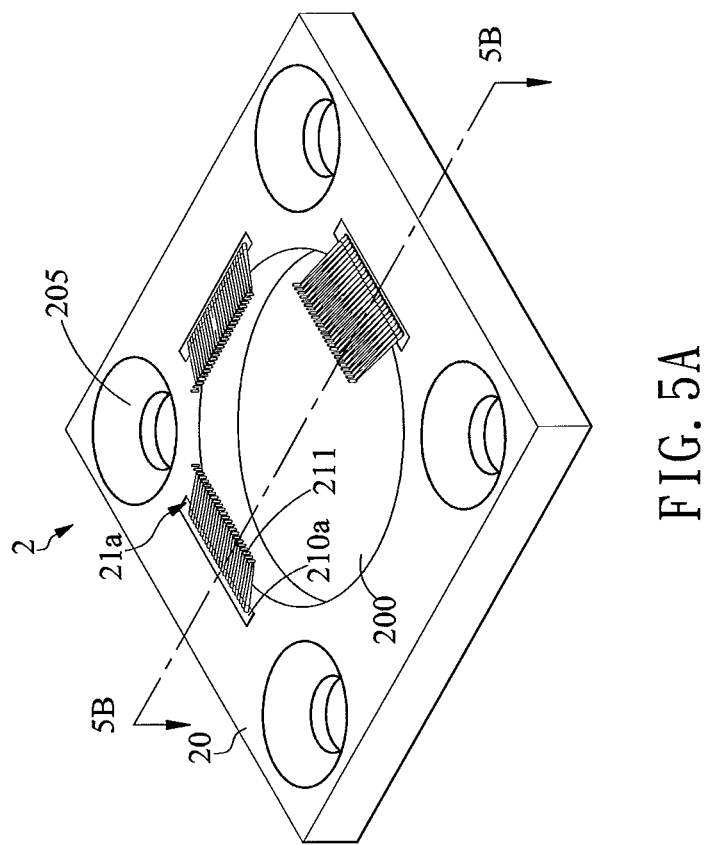
FIG. 5A is a schematic perspective view of a probe holding structure according to another embodiment of the present invention.

Referring to FIG. 2, this figure shows a schematic perspective view of a probe holding structure according to an embodiment of the present invention. In this embodiment, the probe holding structure 2 includes a substrate 20 and a plurality of holding modules 21. Referring to FIG. 3A, this figure shows a schematic perspective view of the substrate according to an embodiment of the present invention. As shown in FIG. 3A, the substrate 20 includes an opening 200 and a plurality of grooves 201, which are arranged around the periphery of the opening 200 and penetrate through the body of the substrate 20. These grooves 201 may be arranged, but not limited to, in a U-shaped manner or a rectangle-shaped manner. As shown in FIG. 3A, the grooves 201 are arranged like a U-shaped manner, i.e. the grooves 201 arranged at three sides of the periphery of the opening 200. However, as shown in FIG. 3B that shows a schematic perspective view of the substrate according to another embodiment of the present invention, the grooves 202 of the substrate 20 do not penetrate the body of the substrate 20 but each have a bottom surface 203 on which a plurality of first through holes 204 penetrating the body of the substrate 20 are provided. It is to be mentioned that the substrate 20 provided by these embodiments of the present invention may be made of, but not limited to, engineering plastics, Bakelite or ceramic material. Preferably, the substrate 20 in these embodiments is a ceramic plate. In addition, the substrate 20 shown in FIG. 3A or FIG. 3B is provided with a plurality of countersunk holes 205, the number and position of which can be determined according to the actual dimension and configuration of the substrate 20, not limited to be arranged at the four corners of the substrate 20 as shown in FIGS. 3A and 3B. The purpose of these countersunk holes 205 lies in that when fasteners, such as screws, are used to fasten the substrate 20 to a base seat, the fasteners can be respectively inserted into and sunk within the countersunk holes 205, such that the fasteners will not protrude over the surface of the substrate 20 so as to prevent the chips under test from damage. Though the first through holes 204 in a groove 202 of the aforesaid embodiment are shown as individual through holes, they can be configured to be integrally communicated together to form a single through groove for the pass of the probes according to a modification.

Figure 4:
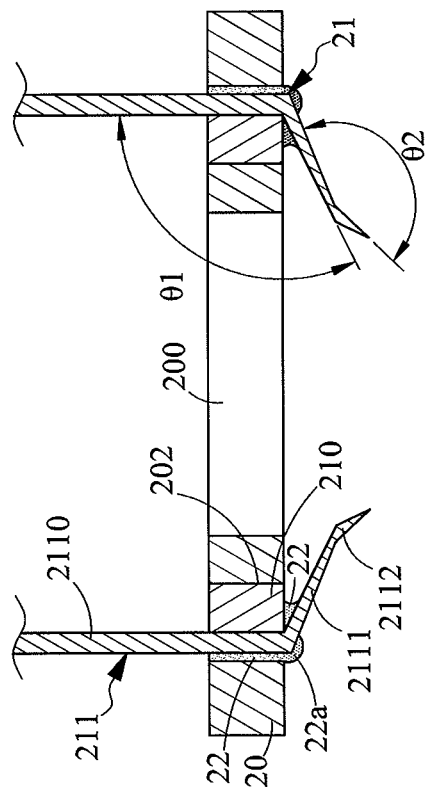
FIG. 4 is a cross-sectional view taken along the line 4-4 of FIG. 2.

Referring to FIGS. 2 and 3B, the substrate 20 used in the embodiment shown in FIG. 2 is the substrate shown in FIG. 3B. As shown in FIG. 2, the holding module 21 are received in and connected with the grooves 202, respectively. Each holding model 21 includes a fixing member 210 and a plurality of probes 211. In this embodiment, each of the fixing members 210 is an elongated prism. The fixing member 210 may be made of, but not limited to, engineering plastics, Bakelite or ceramic material. Preferably, the fixing member 210 in this embodiment is made of ceramic material. Referring to FIG. 4 which is a schematic cross-sectional view of the probe holding structure of FIG. 2, the way of connecting the holding module 21 with the associated groove 202 will be illustrated hereinafter. In this embodiment, each probe 211 is firstly adhered to the fixing member 210 by adhesive 22, such as epoxy resin, such that a single holding module 21 can be obtained. Each probe 211 is bent to form an N-type probe construction having an extension portion 2110, a suspension arm 2111 and a detecting portion 2112. The extension portion 2110 of the probe 211 is abutted at a lateral surface of the fixing member 210 in such a way that the extension portion 2110 is substantially perpendicular to the surface of the substrate 20. The suspension arm 2111 is integrally connected with the extension portion 2110 and defines with the extension portion 2110 a first contained angle θ1. In order to adhesively fasten the probe 211 to the fixing member 210, the suspension arm 2111 is connected with the fixing member 210 through the adhesive 22. The detecting portion 2112 is integrally connected with the suspension arm 2111 and defines with the suspension arm 2111a second contained angle θ2. The degrees of the first and second contained angles θ1 and θ2 are not specifically limited. These contained angles can be set at any desired angle based on the actual need of bending. The arrangement of the suspension arms 2111 of the above-mentioned probes 211 belongs to a probe arrangement of cantilever probe card. After a column of probes 211 have been arranged on the fixing member 210, a next column of probes 211 can be further arranged on the fixing member 210 so as to form a probe arrangement structure having layered columns of suspension arms 2111 arranged on the fixing member 210.

The surface of the fixing member 210 that is contacted with the probes 211 may be, but not limited to, a flat surface. For example, on at least one lateral surface of the fixing member 210, a plurality of recesses may be provided for facilitating positioning and arrangement of the bent probes 211. Referring to FIG. 4 again, each holding module 21 thus obtained is embedded into the corresponding groove 202 of the substrate 20. Because the substrate 20 shown in FIG. 3B is used in this embodiment, the extension portion 2110 of each probe 211 will extend through a corresponding first through hole 204 and protrude out of the substrate 20. Thanks to the design of the first through hole 204, the extension portion 2110 that protrudes out of the substrate 20 can be well positioned for facilitating transmission of the electric signal. In order to fixedly fasten the holding module 21 on the substrate 20, an adhesive 22 can be filled in the gap between the holding module 21 and the groove 202 to enhance the connection strength therebetween after the holding module 21 is received in the corresponding groove 202. In another embodiment, an adhesive 22a may be further used between the suspension arm 2111 of the probe 211 and the substrate 20 to enhance the connection strength therebetween. In addition, it is to be mentioned that in another embodiment the fixing member 210 may not be received in the groove 202 but connected on the surface of the substrate 20 corresponding to the groove 202 directly. In this case, the groove 202 may be a through groove having an opening width smaller than the width of the fixing member 210 for allowing the pass of the corresponding probes only. As for the connection between the fixing member 201 and the substrate 20, it can be achieved by adhesion by using epoxy resin.

Figure 5B:
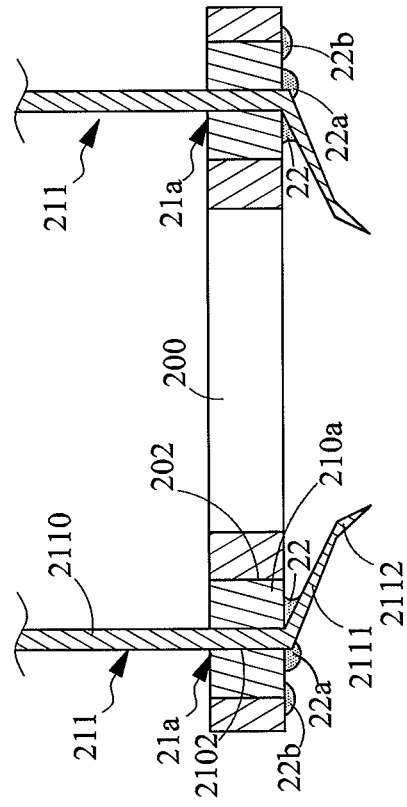
FIG. 5B is a cross-sectional view taken along the line 5B-5B of FIG. 5A.
Figure 6A:
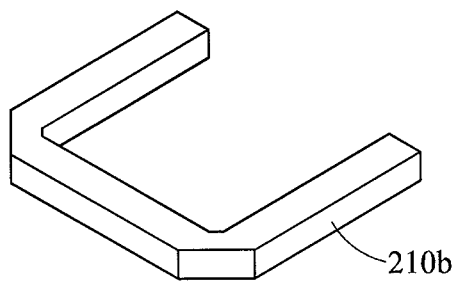
FIGS. 6A and 6B are schematic views showing two alternate forms of the fixing members that are integrally connected and formed in a one-piece construction.
Figure 6B:
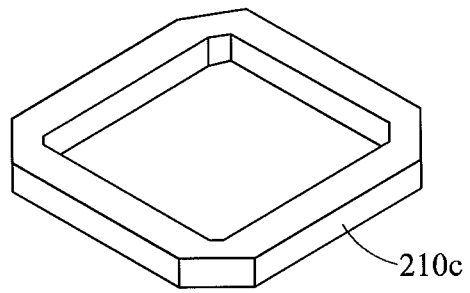

Referring to FIGS. 5A and 5B, FIG. 5A is a schematic perspective view of a probe holding structure according to another embodiment of the present invention, and FIG. 5B is a cross-sectional view taken along the line 5B-5B of FIG. 5A. The probe holding structure disclosed in FIGS. 5A and 5B is basically the same as that of FIG. 2 but with the difference lying in that the fixing member 210a of the holding module 21a is different in structure from the fixing member 210 of FIG. 2. In this embodiment, the fixing member 210a has a plurality of through holes 2102 corresponding to the probes 211 for the passing therethrough the extension portions 2110 of the probes 211 respectively. As shown in FIG. 5B, after the probes 211 are inserted through the fixing member 210a, the probes 211 can be fixedly adhered to the fixing member 210a by the adhesive 22 and the adhesive 22a. It is to be understood that the locations that the adhesive 22 and the adhesive 22a are applied to can be elected according to the actual need and are not limited to the locations disclosed in FIG. 5B. Thereafter, the whole holding module 21a is embedded into the corresponding groove of the substrate 20. The groove of the substrate 20 can be selected from the groove 201 of FIG. 3A or the groove 202 of FIG. 3B. In this embodiment, the groove 202 of FIG. 3B is used. When the whole holding module 21a is embedded into the corresponding groove 202, an adhesive 22b can be further applied at the conjunction between the holding module 21a and the substrate 20 to enhance the connection strength between the holding module 21a and the substrate 20. It is to be understood that the location that the adhesive 22b, through which the holding module 21a is connected with the substrate 20, is applied to is not limited to the one shown in this embodiment. A suitable conjunction can be always selected, based on the actual need, for application of the adhesive so as to enhance the connection strength. The aforesaid through holes 2102 are individual through holes in the embodiment; however, they can be modified to be communicated together so as to form a single through groove for the pass of the probes. Because the probe holding structure of the present invention comprises the holding module that is an individual element from the substrate and can be detachably mounted to the substrate, the work of installing probes to form the probe holding module and the work of mounting the probe holding module to the substrate can be carried out separately, thereby increasing the efficiency of assembling. In addition, the probe holding modules can be individually detached from the substrate during replacing the probes, such that the problem of discarding the whole probe holding structure having problematic probes of the prior art and the cost increased due to this problem can be avoided. Further, in the embodiments shown in FIG. 2 and FIG. 5A, the fixing members 210 of the holding modules 21 of FIG. 2 and the fixing members 210a of the holding modules 21a of FIG. 5A are elongated prisms individually. In another embodiment, as shown in FIGS. 6A and 6B, the fixing members are configured to be integrally connected with each other to form a ring-like construction, such as a one-piece construction having a rectangle-shaped or U-shaped configuration. That is, FIG. 6A shows a fixing member 210b having a U-shaped configuration and FIG. 6B shows a fixing member 210c having a rectangle-shaped configuration. These fixing members shown in FIGS. 6A and 6B can serve as the fixing members for the holding modules of FIG. 2. Furthermore, in another embodiment, the U-shaped fixing member 210b of FIG. 6A and the rectangle-shaped fixing member 210c of FIG. 6B can be configured having through holes such that they can be used as the fixing members of the holding module of FIG. 5A.

Figure 7:
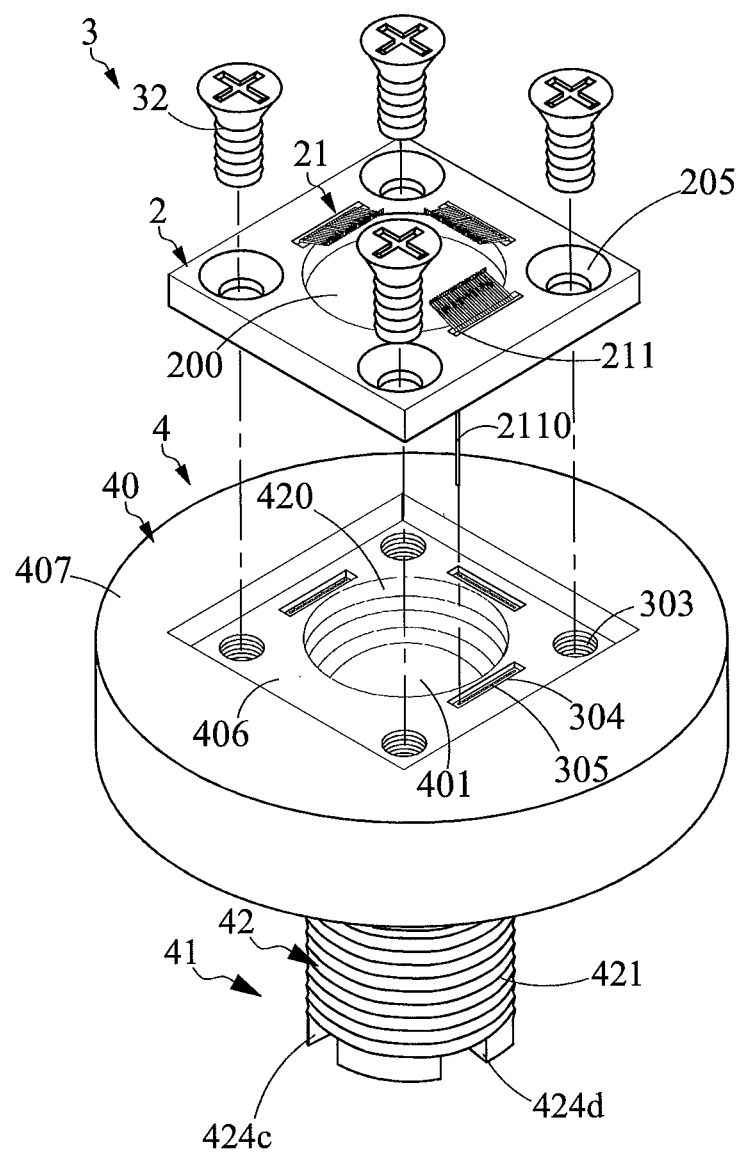
FIG. 7 is an exploded view of an optical inspection device according to an embodiment of the present invention.
Figure 8B:
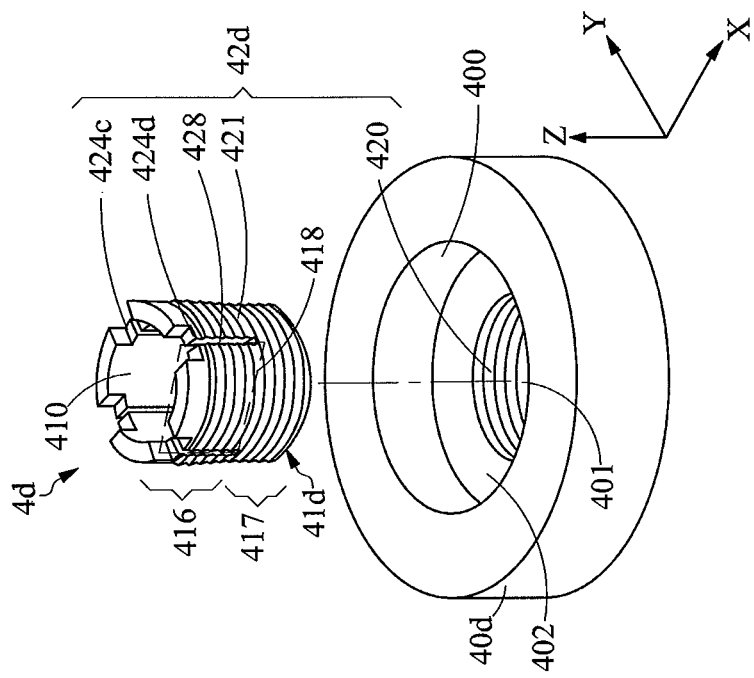
FIGS. 8A to 8C are schematic perspective views of the lens adjusting mechanisms according to various embodiments of the present invention.
Figure 8A:
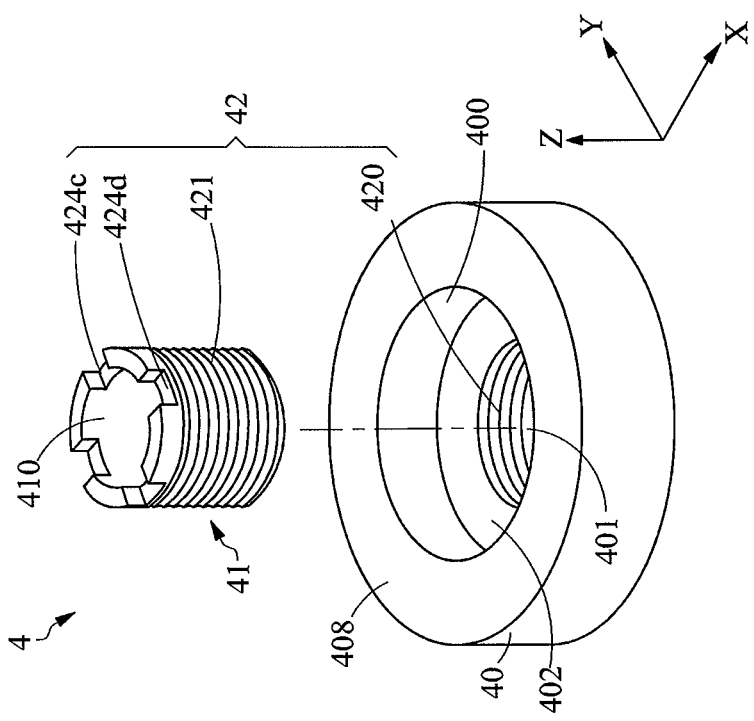

Referring to FIGS. 7 and 8A, FIG. 7 is an exploded view of an optical inspection device of the present invention, and FIG. 8A is a schematic perspective view showing a base seat and a lens holder of a lens adjusting mechanisms of the optical inspection device of FIG. 7 according to an embodiment of the present invention. As shown in the drawings, the optical inspection device 3 is composed of a probe holding structure 2 and a lens adjusting mechanism 4 including a base seat 40, a lens holder 41 and a position adjusting structure 42. The base seat 40 has a first opening 401. On a first surface 407 of the base seat 40, a second accommodation 406 is recessedly provided for receiving the probe holding structure 2. The first opening 401 is configured penetrating the body of the base seat 40 and communicated with the second accommodation 406 in such a manner that the first opening 401 is in alignment with the second opening 200 of the corresponding probe holding structure 2. On the bottom surface of the second accommodation 406, a plurality of threaded holes 303 are provided. In this embodiment, the threaded holes 303 are located at four corners of the bottom surface of the second accommodation 406 and aimed at the four countersunk holes 205 of the probe holding structure 2, respectively. A plurality of grooves 304 are further provided on the bottom surface of the second accommodation 406 and correspond in location to the holding modules 21, respectively. Each of the grooves 304 has a bottom surface, on which a plurality of through holes 305 penetrating the body of the base seat 40 are provided in such a manner that these through holes 305 correspond in location to the probes 211 of one of the holding module 21, respectively. In this way, the extension portion 2110 of each probe 211 can pass through the corresponding through hole 305 and then be electrically connected with the contact pad on the surface of a circuit board of the probe card.

The base seat 40 includes an annular recess 400 on a second surface 408 opposite to the first surface 407. The annular recess 400 surrounds around and is communicated with the first opening 401 penetrating the body of the base seat 40. It is to be mentioned that the annular recess 400 provided in this embodiment is just an exemplary construction for the base seat, i.e. the base seat 40 may be configured without the annular recess 400. For example, in another embodiment, the base seat 40 is configured having the first opening 401 penetrating the body of the base seat 40 without the recess 400. In the embodiment of FIG. 8A, a flange 402 is formed around the periphery of the first opening 401. The lens holder 41 is coupled into the first opening 401. The lens holder 41 has a cylindrical configuration with an accommodation 410 for accommodating a lens therein. In this embodiment, the lens holder 41 has a thread formed on the wall surface surrounding the accommodation 410 for being screwingly engaged with the lens.

The position adjusting structure 42 is provided at between the lens holder 41 and the first opening 401 and operatable to allow the lens holder 41 to do a position adjusting motion in the first opening 401 along the Z-axis direction. In this embodiment, the position adjusting structure 42 includes a first thread 420 formed on the inner wall surface of the base seat 40 surrounding the first opening 401, a second thread 421 formed on the outer wall surface of the lens holder 41 and screwingly engageable with the first thread 420, and two pairs of adjustment notches 424c and 424d formed on the top surface of the lens holder 41 and symmetrically arranged around the opening of the accommodation 410. In this embodiment, the adverse effect of the backlash between the engaged threads is minimized by increasing the engaging ratio between the first and second threads 420 and 421 or by applying escape-preventing adhesive in between the first thread 420 and the second thread 421 so as to enhance the accuracy of position adjusting motion. In still another embodiment, the engaging ratio of the engaged threads may be increased by using different materials, such as engineering plastics or other metals, to manufacturing the lens holder 41 and the base seat 40. In this embodiment, the lens holder 41 and the base seat 40 may be made having different hardness, i.e. the hardness of the base seat 40 is greater than that of the lens holder 41 or vice versa, so as to enhance the engaging ratio of the engaged threads. Preferably, the base seat 40 is made having a hardness greater than that of the lens holder 41 in this embodiment. In addition, the thickness D defined between the inner wall surface defining the accommodation 410 and the outer wall surface of the lens holder 41 corresponding in location to the accommodation 410 satisfies the equation $0.5 \text{ mm} \leq D \leq 1.5 \text{ mm}$.

The way of how to adjust the position of the lens holder 41 shown in FIGS. 7 and 8A is further described hereinafter. Since two pairs of adjustment notches 424c and 424d are provided in this embodiment, the operator can easily control the lens holder 41 to move downward or upward in the Z-axis direction by engaging a cross-shaped jig with the two pairs of the adjustment notches 424c and 424d and then driving the lens holder 41 to turn clockwise or counterclockwise. It is to be understood that the number and the arrangement of the adjustment notches are not limited to the disclosure in this embodiment though there are two pairs of the adjustment notches 424c and 424d shown in this embodiment. For example, at least one engagement notch or one pair of engagement notches may be used for a person skilled in the art based on the design spirit of this embodiment. In the case that one adjustment notch or a pair of adjustment notches are used, the operator can engage a linear-shaped jig with the adjustment notch or the pair of engagement notches and then drive the lens holder 41 to turn. In addition, in another embodiment, the flange 402 of the base seat 40 can be eliminated, such that the total volume of the lens adjusting mechanism 4 can be further reduced.

FIG. 8B shows a schematic perspective view of the lens adjusting mechanism according to another embodiment of the present invention. In this embodiment, the lens adjusting mechanism 4d comprises a base seat 40d, a lens holder 41d and a position adjusting structure 42d. The base seat 40d, the lens holder 41d and the position adjusting structure 42d are basically the same as those disclosed in FIG. 8A; however, the difference therebetween lies in that the outer wall surface of the lens holder 41d is divided into a first zone 416 and a second zone 417, and the position adjusting structure 42d further comprises a plurality of slits 428 equiangularly formed at the body of the first zone 416 of the lens holder 41d, such that the first zone 416 of the lens holder 41d is configured having a plurality of engagement adjusting portions 418 expanding inclinedly and outwardly. As a result, the diameter of the first zone 416 having a part of the second thread 421 is gradually decreased from the top to the bottom of the first zone 416; however, the diameter of the second zone 417 having the other part of the second thread 421 maintains constant.

The way of how to adjust the position of the lens holder 41d having two pairs of adjustment notches 424c and 424d shown in FIG. 8B is same as that of the embodiment shown in FIG. 8A; therefore, the detailed description in this matter is not repeatedly illustrated hereunder. In this embodiment, a part of the second thread 421 is distributed on the first zone 416 of the lens holder 41d, the other part of the second thread 421 is distributed on the second zone 417 of the lens holder 41d, and the first zone 416 has a diameter greater than that of the second zone 417; therefore, when the lens holder 41d is screwingly engaged with the base seat 40d through the engagement of the second thread 421 on the second zone 417 with the first thread 420 and continuously moves downwards to allow the second thread 421 on the engagement adjusting portions 418, i.e. the first zone 416, to engage with the first thread 420, the outwardly expanded engagement adjusting portions 418 will be restricted and compressed by the first opening 401 of the base seat 40d to contract toward inside of the opening of the accommodation 410 of the lens holder 41d as the lens holder 41d continuously moves downward, and meanwhile the slits 428 provide sufficient buffer spaces needed for compression. By means of aforesaid compression action, each engagement adjusting portion 418 produces an outward thrust exerting on the wall of the first opening 401, such that the second thread 421 can be firmly engaged with the first thread 420 to prevent the adverse effect of the backlash between engaged threads as the lens holder 41d moves upwards and downwards, thereby enhancing the accuracy of the position adjusting motion.

Figure 8C:
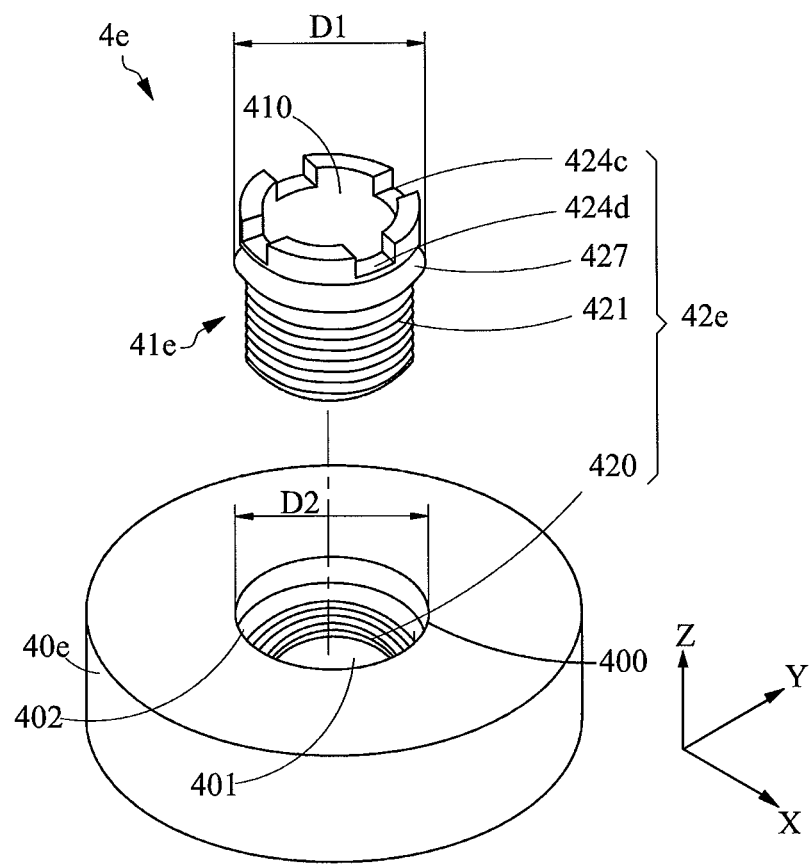

FIG. 8C shows a schematic perspective view of the lens adjusting mechanism according to still another embodiment of the present invention. In this embodiment, the lens adjusting mechanism 4e comprises a base seat 40e, a lens holder 41e and a position adjusting structure 42e. The base seat 40e, the lens holder 41e and the position adjusting structure 42e are basically the same as those disclosed in FIG. 8A; however, the difference therebetween lies in that the position adjusting structure 42e further comprises a flexible ring 427, such as but not limited to O-ring, which is sleeved onto the lens holder 41e and located at the topmost portion of the second thread 421. The outer diameter D1 of the flexible ring 427 may be greater than or equal to the caliber D2 of the annular recess 400; therefore, when the lens holder 41e is threaded with the base seat 40e, the flexible ring 427 will be jammed by the wall of the annular recess 400 to make lens holder 41e and the annular recess 400 be tightly connected with each other, thereby enhancing the securing effect of the lens holder 41e to the base seat 40e. In this embodiment, the caliber D2 of the annular recess 400 is greater than the caliber of the first opening 401 as shown in FIG. 8C. In still another embodiment of the present invention, the caliber D2 of the annular recess 400 may be equal to that of the first opening 401 according to the actual need.

The way of how to adjust the position of the lens holder 41e having two pairs of adjustment notches 424c and 424d shown in FIG. 8C is same as that of the embodiment shown in FIG. 8A; therefore, the detailed description in this matter is not repeatedly illustrated hereunder. When the second thread 421 is engaged with the first thread 420 provided on the wall of the first opening 401 and the lens holder 41e is moved downward in Z-axis direction by tuning the lens holder 41e clockwise, the flexible ring 427 will contact and then be squeezed by the wall of the annular recess 400 to deform as the lens holder 41e is continuously moved downward, such that the flexible ring 427 will be tightly connected with the annular recess 400, and the rebound force produced by the compressed flexible ring 427 will exert on the wall of the annular recess 400 to make the lens holder 41e equipped with the flexible ring 427 be more tightly connected with the base seat 40e than a lens holder without the flexible ring 427. Under the condition that the flexible ring 427 is tightly connected with the annular recess 400, as the lens holder 41e is moved upwards and downwards, the adverse effect of the backlash between the engaged first and second threads 420 and 421 will be minimized due to the function of the flexible ring 427, thereby reducing the slip of the lens holder 41e during movement of the lens holder 41e. As a result, the position of the lens holder 41e can be precisely controlled when the lens holder 41e is moved upwards and downwards.

It is to be mentioned that in the embodiments shown in FIGS. 8A to 8C, the base seat is in cooperation with one lens adjusting mechanism; however, the present invention is not limited to the disclosures shown in these figures. In still another embodiment, the base seat may be configured to be equipped with a plurality of lens adjusting mechanisms based on the actual need and the design spirit of the present invention, as shown in FIG. 9A or FIG. 9B.

Referring to FIG. 7 again, the probe holding structure 2 shown in FIG. 2 or FIG. 5A can be used in this embodiment. By means of inserting fasteners 32, such as screws, through the countersunk holes 205 and then engaging the fasteners 32 into the threaded holes 303 respectively, the probe holding structure 2 is fixedly fastened in the second accommodation 406 of the base seat 40. During chip testing, an external light source may be used to project light on the chip under test to make the chip under test produce electric signals. After the probes 211 contacting the chip under test receive the electric signals, the signals will be transmitted through the extension portions 2110 of the probes 211 to the contact pads of the circuit board, which will in turn be transmitted from the circuit board to a tester for further processing. Since the lens holder 41 is screwingly coupled into the first opening 401 and the first opening 401 is aligned with the second opening 200 of the probe holding structure 2, the lens disposed inside the lens holder 41 can receive light through the second opening 200 to make the optical inspection on the device under test possible.

Figure 9A:
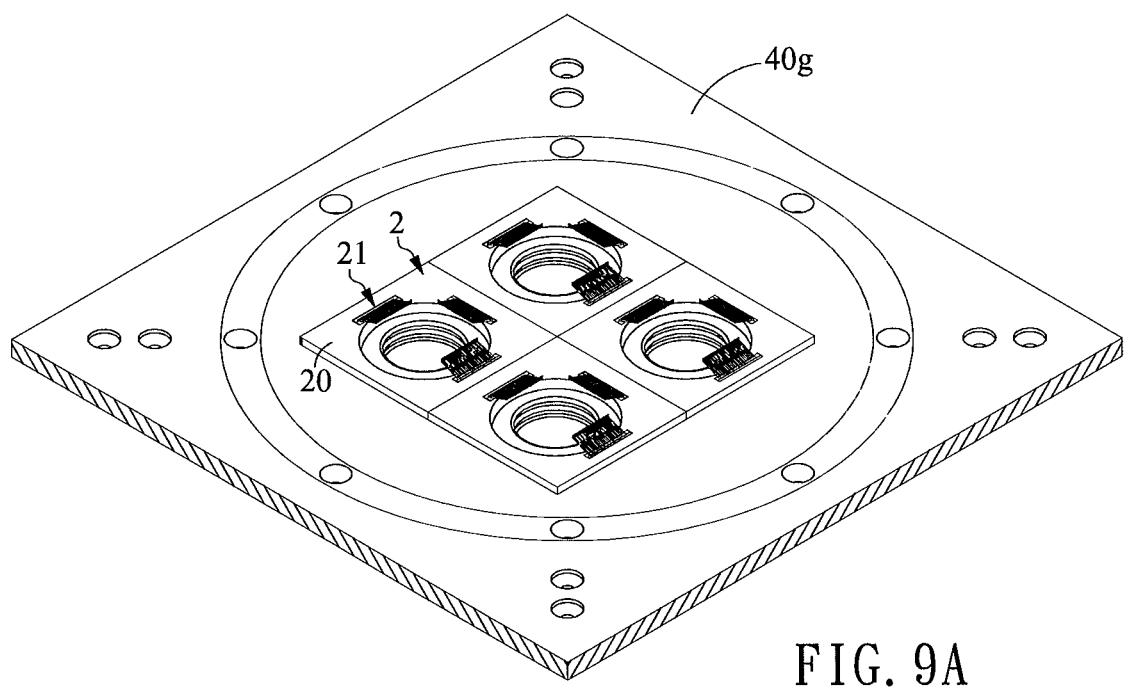
FIGS. 9A and 9B are schematic perspective views respectively showing that the probe holding structures are arranged in a matrix format.
Figure 9B:
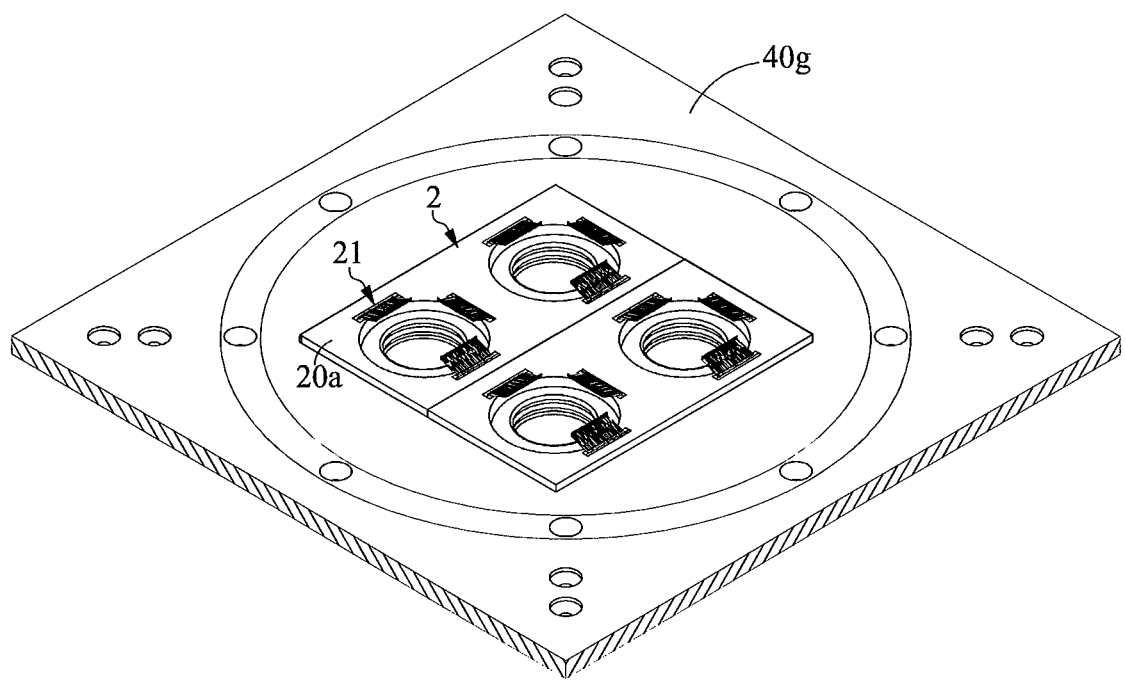

The base seat 40 disclosed in FIG. 7 is configured to be in cooperation with a single probe holding structure 2; however, the base seat can be configured to be mounted with a plurality of probe holding structures as shown in FIGS. 9A and 9B. FIGS. 9A and 9B are schematic drawings respectively showing that a plurality of probe holding structures are arranged in a matrix format. In the embodiments shown in FIGS. 9A and 9B, the probe holding structures 2 are mounted on the base seat 40g in a manner of two-dimensional matrix arrangement. Each probe holding structure 2 may correspond to one or more lens holders. In FIG. 9A, each substrate 20 is mounted with a plurality of holding modules 21 arranged in a single U-shaped manner; however, in FIG. 9B, a plurality of holding modules 21 are arranged on a signal substrate 20a in a plurality of U-shaped manners. These modifications are made based on the design spirit of the present invention.

Figure 10:
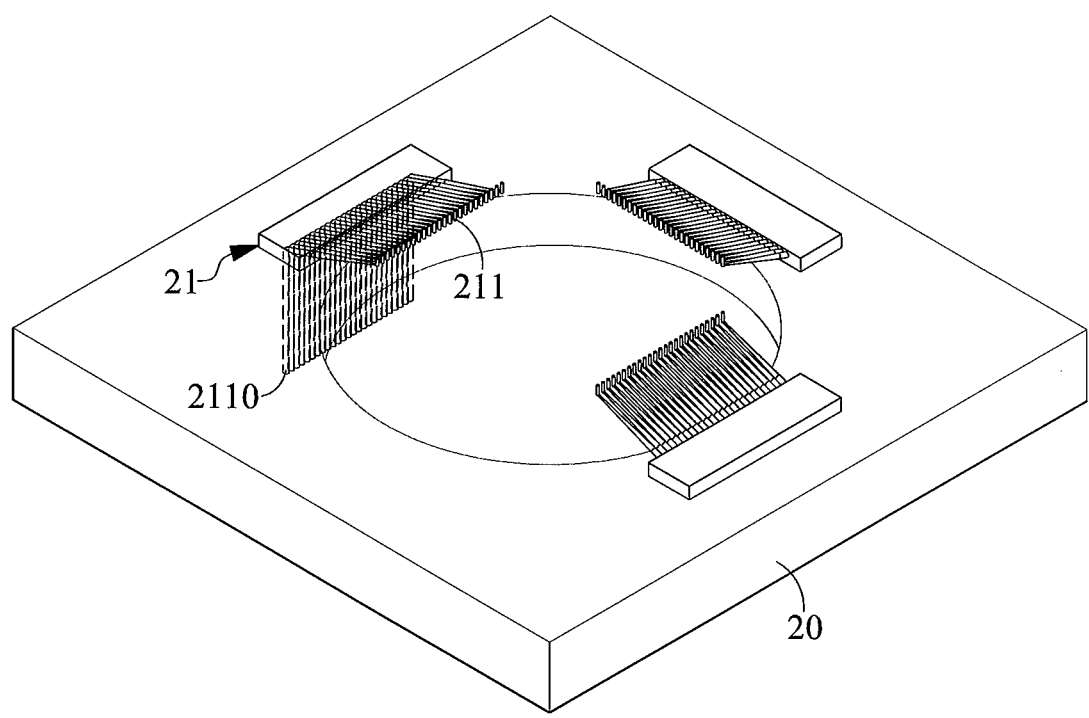
FIG. 10 is a schematic perspective view of a probe holding structure according to still another embodiment of the present invention showing the way of installing the probes.

FIG. 10 is a schematic perspective view of a probe holding structure according to still another embodiment of the present invention showing the way of installing the probes. Based on the construction of the holding modules 21 having a plurality of probes 211 shown in FIGS. 9A and 9B, the probes are arranged as an N-type probe arrangement, i.e. each probe 211 has an extension portion 2110 set in a posture substantially perpendicular to the substrate 20.

Although particular embodiments of the invention have been described in detail for purposes of illustration, various modifications and enhancements may be made without departing from the spirit and scope of the invention. Accordingly, the invention is not to be limited except as by the appended claims.

What is claimed is:
1. A probe holding structure comprising:
a substrate having an opening and a plurality of grooves arranged around a periphery of the opening, the opening being configured to al low a light from an external light source to pass therethrough; and
a plurality of holding modules connected with the grooves respectively; each of the holding modules comprising:
a fixing member connected with a corresponding said groove; and
a plurality of probes connected with the fixing member and passing through the corresponding said groove.
2. The probe holding structure as claimed in claim 1, wherein the grooves penetrate through a body of the substrate; each of the holding modules is received in one of the grooves.
3. The probe holding structure as claimed in claim 2, wherein each of the probes comprises:
an extension portion abutted at a lateral surface of the fixing member and passing through the corresponding said groove;
a suspension arm connected with the extension portion and defining with the extension portion a first contained angle; and
a detecting portion connected with the suspension arm and defining with the suspension arm a second contained angle;
wherein an adhesive is applied between the suspension portion and the fixing member.
4. The probe holding structure as claimed in claim 1, wherein each of the probes comprises:
an extension portion abutted at a lateral surface of the fixing member and passing through the corresponding said groove;
a suspension arm connected with the extension portion and defining with the extension portion a first contained angle; and
a detecting portion connected with the suspension arm and defining with the suspension arm a second contained angle;
wherein an adhesive is applied between the suspension portion and the fixing member.
5. The probe holding structure as claimed in claim 1, wherein the grooves of the substrate are communicated together.

6. The probe holding structure as claimed in claim 5, wherein the fixing members of the holding modules are connected together to form a one-piece fixing structure.

7. The probe holding structure as claim in claim 6, wherein the grooves of the substrate penetrate through a body of the substrate and are communicated together; the one-piece fixing structure is connected on a surface of the substrate corresponding to the communicated grooves; each of the probes passes through the corresponding said groove.

8. The probe holding structure as claim in claim 6, wherein the one-piece fixing structure has a rectangle-shaped or U-shaped configuration.

9. The probe holding structure as claimed in claim 1, wherein the fixing members of the holding modules are connected together to form a one-piece fixing structure.

10. The probe holding structure as claim in claim 9, wherein the grooves of the substrate penetrate through a body of the substrate and are communicated together; the one-piece fixing structure is connected on a surface of the substrate corresponding to the communicated grooves; each of the probes passes through the corresponding said groove.

11. The probe holding structure as claim in claim 9, wherein the one-piece fixing structure has a rectangle-shaped or U-shaped configuration.

12. An optical inspection device comprising:
a lens adjusting mechanism comprising:
  a base seat having at least one first opening; and
  at least one lens holder received in the at least one first opening respectively and each having an accommodation for accommodating a lens; and
at least one probe holding structure disposed on a surface of the base seat and each comprising:
  a substrate having a second opening aligned with the first opening and a plurality of grooves arranged around a periphery of the second opening, the second opening being configured to allow a light from an external light source to pass therethrough; and
  a plurality of holding modules connected with the grooves respectively; each of the holding modules comprising:
    a fixing member connected with a corresponding said groove; and
    a plurality of probes connected with the fixing member and passing through the corresponding said groove.

13. The optical inspection device as claimed in claim 12, wherein the grooves penetrate through a body of the substrate; each of the holding modules is received in one of the grooves.

14. The optical inspection device as claimed in claim 13, wherein each of the probes comprises:
an extension portion abutted at a lateral surface of the fixing member and passing through the corresponding said groove;
a suspension arm connected with the extension portion and defining with the extension portion a first contained angle; and
a detecting portion connected with the suspension arm and defining with the suspension arm a second contained angle;
wherein an adhesive is applied between the suspension portion and the fixing member.

15. The optical inspection device as claimed in claim 12, wherein each of the probes comprises:
an extension portion abutted at a lateral surface of the fixing member and passing through the corresponding said groove;
a suspension arm connected with the extension portion and defining with the extension portion a first contained angle; and
a detecting portion connected with the suspension arm and defining with the suspension arm a second contained angle;
wherein an adhesive is applied between the suspension portion and the fixing member.

16. The optical inspection device as claimed in claim 12, wherein the grooves of the substrate are communicated together.

17. The optical inspection device as claimed in claim 16, wherein the fixing members of the holding modules are connected together to form a one-piece fixing structure.

18. The optical inspection device as claimed in claim 17, wherein the grooves of the substrate penetrate through a body of the substrate and are communicated together; the one-piece fixing structure is connected on a surface of the substrate corresponding to the communicated grooves; each of the probes passes through the corresponding said groove.

19. The optical inspection device as claimed in claim 17, wherein the one-piece fixing structure has a rectangle-shaped or U-shaped configuration.

20. The optical inspection device as claimed in claim 12, wherein the fixing members of the holding modules are connected together to form a one-piece fixing structure.

21. The optical inspection device as claimed in claim 20, wherein the grooves of the substrate penetrate through a body of the substrate and are communicated together; the one-piece fixing structure is connected on a surface of the substrate corresponding to the communicated grooves; each of the probes passes through the corresponding said groove.

22. The optical inspection device as claimed in claim 20, wherein the one-piece fixing structure has a rectangle-shaped or U-shaped configuration.

23. The optical inspection device as claimed in claim 12, wherein the base seat is provided at the surface thereof with at least one second accommodation for accommodating the at least one probe holding structure; the first opening of the base seat is configured penetrating a body of the base seat and communicated with the accommodation of the base seat in a way that the first opening is in alignment with the second opening of the corresponding probe holding structure.

24. The optical inspection device as claimed in claim 12, further comprising at least one position adjusting structure configured corresponding to the at least one first opening and the at least one lens holder and formed with the base seat and the at least one lens holder for enabling the at least one lens holder to do a position adjusting motion in the at least one first opening; wherein the lens holder has at least one adjustment notch provided at a top surface of the lens holder at a periphery of an opening of the accommodation of the lens holder; wherein each said position adjusting structure comprises:
a first thread formed on a wall surface of the base seat defining one said first opening;
a second thread formed on an outer wall surface of one said lens holder for engaging with the first thread; and
a flexible ring sleeved onto one said lens holder;
wherein the base seat is provided with an annular recess surrounding around and communicating with the first opening; wherein an outer diameter of the flexible ring is greater than or equal to a caliber of the annular recess, such that the flexible ring is compressed by and tightly connected with a wall of the annular recess when each said lens holder is screwingly engaged with the base seat.

* * * * *